United States Patent [19]

Matsutani

[11] Patent Number: 5,100,432
[45] Date of Patent: Mar. 31, 1992

[54] SURGICAL SUTURE NEEDLE OF THE TAPER POINT TYPE

[75] Inventor: Masaaki Matsutani, Tochigi, Japan

[73] Assignee: Matsutani Seisakusho Co., Ltd., Tochigi, Japan

[21] Appl. No.: 641,917

[22] Filed: Jan. 16, 1991

[30] Foreign Application Priority Data

Feb. 22, 1990 [JP] Japan ................................. 2-39722

[51] Int. Cl.⁵ ............................................ A61B 17/00
[52] U.S. Cl. ..................................... 606/223; 606/224
[58] Field of Search ........................ 606/223, 221, 225

[56] References Cited

U.S. PATENT DOCUMENTS

| | | |
|---|---|---|
| 2,841,150 | 7/1958 | Riall . |
| 3,038,475 | 6/1962 | Orcutt . |
| 3,160,157 | 12/1964 | Chisman ............................. 606/223 |
| 3,892,240 | 7/1975 | Park . |
| 4,957,502 | 9/1990 | Takase . |

FOREIGN PATENT DOCUMENTS

| | | |
|---|---|---|
| 286438 | 10/1988 | European Pat. Off. . |
| 2063327 | 7/1971 | France . |
| 63-309338 | 12/1988 | Japan . |
| 752443 | 7/1956 | United Kingdom . |

Primary Examiner—Stephen C. Pellegrino
Assistant Examiner—Gary Jackson
Attorney, Agent, or Firm—Wegner, Cantor, Mueller & Player

[57] ABSTRACT

A surgical suture needle of the taper point type includes a proximal end portion defining a gut-mounting portion having a hole to which a gut is to be attached, an intermediate portion defining a main body portion having a generally uniform cross-sectional area throughout an entire length thereof, and a distal end portion defining a tapered portion whose cross-sectional area decreases progressively toward a distal end of the suture needle which is pointed. In order to enhance the ability of the suture needle to pierce into an artificial blood vessel, the length of the tapered portion is not less than 9D where D represents a diameter of an imaginary circle having the same cross-sectional area as that of the main body portion. Also, in view of the bending strength of the suture needle, the length of the tapered portion is less than ⅔L where L represents the overall length of the suture needle.

3 Claims, 2 Drawing Sheets

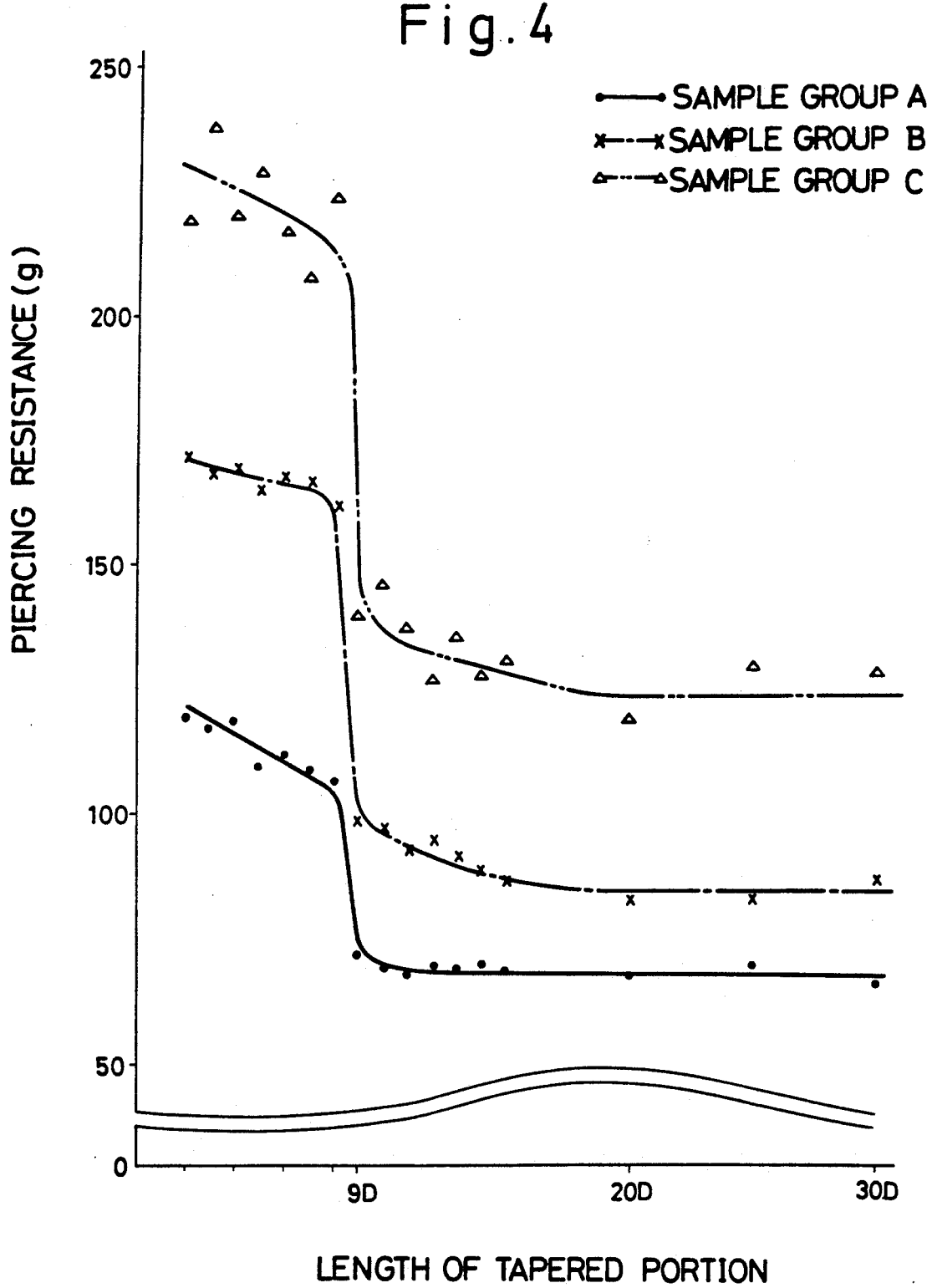

SURGICAL SUTURE NEEDLE OF THE TAPER POINT TYPE

BACKGROUND OF THE INVENTION

This invention relates to a surgical suture needle called "taper point-type."

A surgical suture needle of the taper point type, as disclosed in Japanese Laid-Open (Kokai) Patent application No. 309338/88, includes a proximal end portion defining a gut-mounting portion having a hole to which a gut is to be attached, an intermediate portion defining a main body portion having a generally uniform cross-sectional area throughout an entire length thereof, and a distal end portion defining a tapered portion whose cross-sectional area decreases progressively toward a pointed distal end of the suture needle. The tapered portion has no cutting edge.

The suture needle of the taper point type is caused to pierce the tissue, forcibly opening the tissue without cutting the tissue. A hole formed in the tissue as a result of the piercing of the suture needle therethrough is contracted or reduced in diameter after the passage of the suture needle therethrough, and a gut following the suture needle is brought into intimate contact with the inner periphery of this hole. Therefore, the suture needle of this type is used mainly for suturing the blood vessel.

In conventional suture needles of the taper point type, the tapered portion is short, and its length is about 2 to 7 times greater than the diameter of the main body portion. There are two reasons for this which are mentioned in the following.

Firstly, when the tapered portion is to be formed by grinding, the amount of grinding is intended to be reduced so as to shorten the time required for the grinding, thereby lowering the manufacturing cost.

Secondly, the resistance of the suture needle to the piercing through the blood vessel of the living body greatly depends on the degree of sharpness of the pointed end of the suture needle, and hardly depends on the amount (hereinafter referred to as "cross-sectional area increase rate") of increase of the cross-sectional area of the tapered portion per unit length from the pointed end toward the main body portion. Therefore, even if the tapered portion is made short, the piercing properties of the suture needle are not adversely affected. More specifically, the piercing resistance which the suture needle receives from the blood vessel of the living body is at the maximum level when piercing the skin of the blood vessel. This is due to the fact that the skin of the blood vessel has a greater rupture strength than the other parts of the blood vessel, and also due to the fact that the blood vessel of the living body has elasticity. The resistance of the suture needle to the piercing through the skin of the blood vessel greatly depends on the degree of sharpness of the point end of the suture needle. Once the suture needle pierces the skin of the blood vessel, the piercing resistance is abruptly reduced regardless of the value of the cross-sectional area increase rate of the tapered portion.

However, the above conventional suture needle of the taper point type has an inferior ability to pierce an artificial blood vessel which has been developed recently. This artificial blood vessel is formed by applying a special stretching process to polytetrafluoroethylene (PTFE), and is of an open-cell porous construction, and has the average pore size of about 30 micron meters, that is, has a fibril length of about 30 micron meters. It has been confirmed that such an artificial blood vessel has an excellent compatibility with the living body, and can withstand the blood pressure for a long period of time.

SUMMARY OF THE INVENTION

It is an object of this invention to provide a surgical suture needle which has an excellent ability to pierce an artificial blood vessel.

According to the present invention, there is provided a surgical suture needle of the taper point type including a proximal end portion defining a gut-mounting portion having a hole to which a gut is to be attached, a distal end portion defining a tapered portion whose cross-sectional area decreases progressively toward a distal end of the suture needle which is pointed, and an intermediate portion disposed between the gut-mounting portion and the tapered portion and defining a main body portion having a generally uniform cross-sectional area throughout an entire length thereof, the length of the tapered portion being in the range of between not less than 9D and less than 2/3L where D represents a diameter of an imaginary circle having the same cross-sectional area as that of the main body portion, and L represents the overall length of the suture needle.

BRIEF DESCRIPTION OF THE DRAWINGS

FIG. 4 is a graph showing results of tests with respect to the resistance of suture needles to the piercing through an artificial blood vessel.

DESCRIPTION OF THE PREFERRED EMBODIMENT OF THE INVENTION

Figure 1:
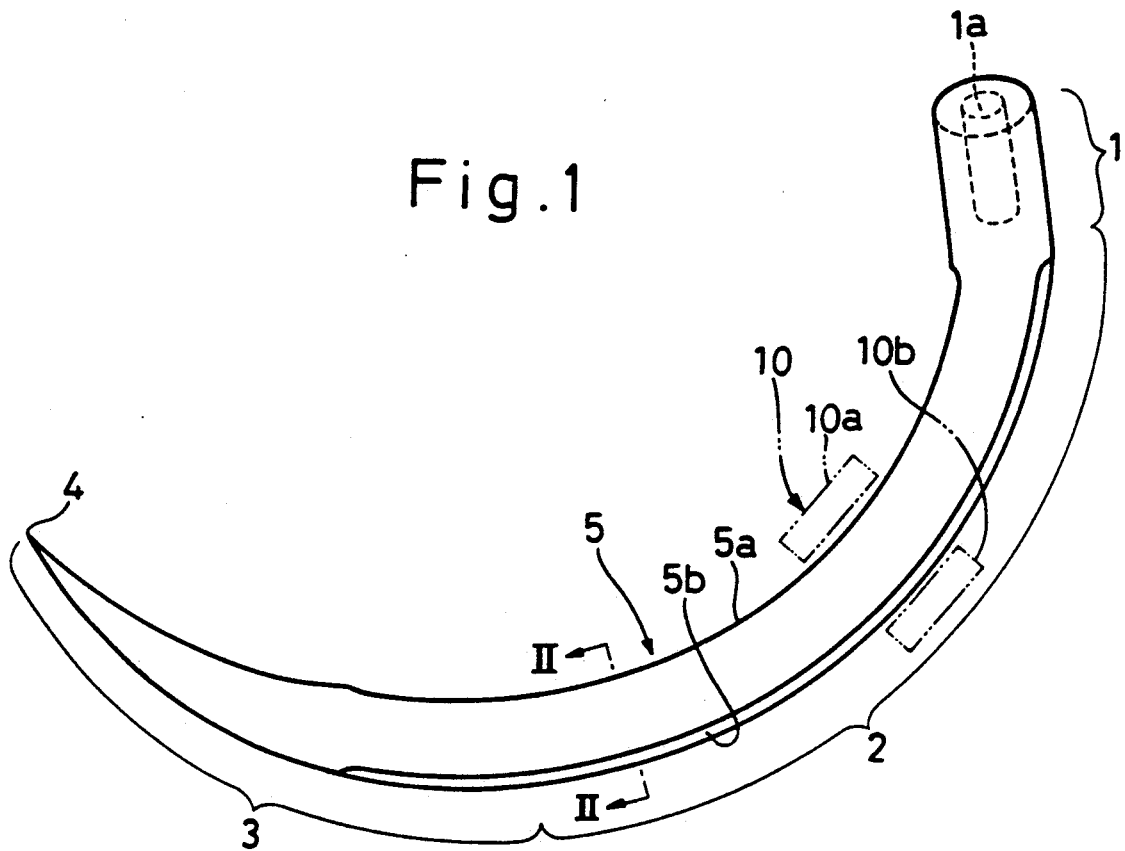
FIG. 1 is a perspective view of a taper point-type suture needle of the present invention, with its thickness shown on an exaggerated scale.

The invention will now be described with reference to the drawings. A suture needle of the taper point type shown in FIG. 1 includes a proximal end portion defining a gut-mounting portion 1, an intermediate portion defining a main body portion 2 having a generally uniform cross-sectional area throughout an entire length thereof, and a distal end portion defining a tapered portion 3 whose cross-sectional area decreases progressively toward a pointed distal end 4 of the suture needle.

The gut-mounting portion 1 is straight, and has a blind hole 1a extending from a proximal end face of the suture needle along the axis thereof. The length of the gut-mounting portion 1 is generally equal to or slightly greater than the length of the hole 1a. A gut (not shown) is inserted at one end portion into the hole 1a, and then the gut-mounting portion 1 is deformed or compressed to hold the gut. Therefore, the gut-mounting portion 1 in its final form is smaller in diameter than that shown in FIG. 1.

Figure 2:
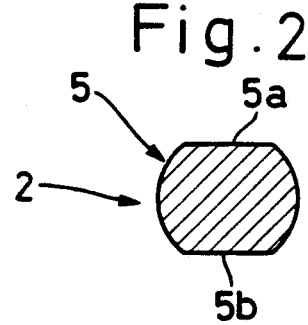
FIG. 2 is a cross-sectional view taken along the line II—II of FIG. 1.

The main body portion 2 as well as the tapered portion 3 is curved. A major proportion of the main body portion 2 and the rear end portion of the tapered portion 3 jointly constitute a continuous grasp portion 5. The grasp portion 5 has a pair of grasp surfaces 5a and 5b which are provided respectively on the inner and outer sides of the curved configuration of the suture needle and are disposed generally parallel to each other. In the transverse cross-section (FIG. 2) through the grasp portion 5, the pair of grasp surfaces 5a and 5b appear as two parallel straight lines. As shown in FIGS. 1 and 2, the grasp portion 5 is flattened. The rear end portion of the main body portion 2 which is not used as the grasp portion 5 has a circular cross-section. The front portion of the tapered portion 3 which is not used as the grasp portion 5 has a generally circular cross-section. Though the tapered portion 3 is varied in cross-section intermediate the opposite ends thereof, the cross-sectional area of the tapered portion 3 is decreasing progressively toward the pointed end 4. In other words, the cross-sectional area of the tapered portion 3 is increasing progressively in a direction away from the pointed end 4. That portion of the main body portion 2 serving as the grasp portion 5 is equal in cross-sectional area to the remainder (i.e., the rear end portion) of the main body portion 2 not used as the grasp portion 5.

Figure 3:
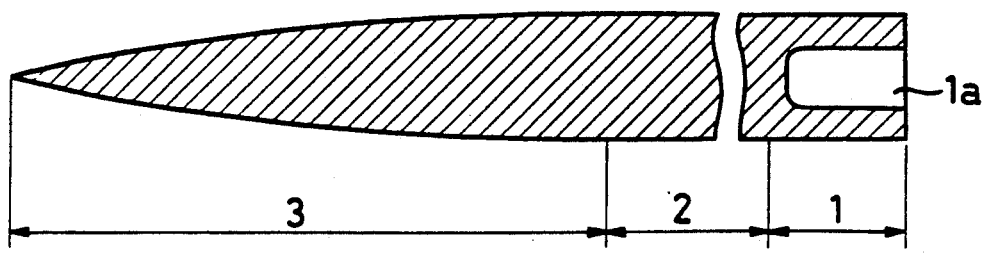
FIG. 3 is a side-elevational view of a portion of a needle material (stock) for the suture needle, with its thickness shown on an exaggerated scale.

A method of producing the suture needle of the above construction will now be described briefly. A wire of austenite-type stainless steel is cold-drawn into a required diameter, with its crystal grains arranged into a fiber-like structure. Then, the wire is cut into a predetermined length to provide a straight stock (needle material), taking a subsequent grinding operation into consideration. Then, the hole 1a (FIGS. 1 and 3) to which a gut is to be attached is formed in one end face of the needle material. Then, the end portion remote from the hole 1a is ground to form the tapered portion 3. As shown in FIG. 3, the surface of the tapered portion 3 bulges outwardly. Strictly speaking, the angle of inclination of the surface of the tapered portion relative to the axis of the needle material is the maximum in the vicinity of the pointed end 4, and is decreasing progressively toward the main body portion 2. In other words, the rate of increase of the diameter and cross-sectional area of the tapered portion 3 toward the main body portion 2 is the maximum at the pointed end 4, and is decreasing progressively toward the main body portion 2. Then, the needle material is pressed to form the grasp surfaces 5a and 5b (FIG. 1). The cross-sectional area of each portion of the needle material is hardly changed by this pressing operation. Therefore, the cross-sectional area increase rate of the tapered portion 3 is hardly influenced by this pressing operation. Then, the needle material is bent to provide the curved tapered portion 3, the curved main body portion 2 and the non-curved gut-mounting portion 1, as shown in FIG. 1. Then, a heat treatment and a surface treatment are applied to the thus bent needle material, and finally a gut is inserted into the hole 1a, and the gut-mounting portion 1 is deformed or compressed so as to fixedly secure the gut thereto.

In the suture needle of the present invention, the length of the tapered portion 3 is not less than nine times greater than the diameter D of the main body portion 2. Here, the diameter D means the diameter of the cross-sectionally circular rear end portion of the main body portion 2 which is not pressed, or the diameter of an imaginary circle having the same cross-sectional area as the cross-sectional area of that portion of the main body portion 2 which is pressed to serve as the grasp portion 5.

The reason why the length of the tapered portion 3 should be not less than nine times greater than 9D has been obtained from the results of the following tests.

First, three sample groups A, B and C each composed of 17 samples (suture needles) were prepared, the samples of the sample groups A, B and C being different from one another in the overall length L of the suture needle and the diameter D of the main body portion 2. More specifically, the 17 samples of the sample group A had the diameter D of 0.33 mm and the overall length L of 13 mm, and were different from one another in the length of the tapered portion 3 in the range of 2D to 30D (an integral multiple of D). The 17 samples of the sample group B had the diameter D of 0.63 mm and the overall length L of 25 mm, and were different from one another in the length of the tapered portion 3 in the range of 2D to 30D. The 17 samples of the sample group C had the diameter D of 0.98 mm and the overall length L of 35 mm, and were different from one another in the length of the tapered portion 3 in the range of 2D to 30D. The diameter of the semi-spherical pointed ends 4 of all the samples was about 20 micron meters, as was the case with an ordinary suture needle used for a blood vessel of a living body. All the sample suture needles were pierced through artificial blood vessels, and their piercing resistances were measured. Results obtained are shown in FIG. 4. More specifically, in each of the three sample groups A, B and C, the sample whose tapered portion 3 had the length of 2D had the maximum piercing resistance, and the piercing resistance was decreased gradually in the order of the samples having their respective tapered portion lengths of 3D, 4D, 5D, 6D, 7D and 8D. And, the sample having the tapered portion length of 9D was abruptly decreased in piercing resistance, as compared with the samples having the tapered portion length of not more than 8D. In the sample group A, those samples having the tapered portion length of 10D to 30D were hardly changed in piercing resistance. In the sample groups B and C, as the tapered portion length increased from 10D to 20D, the piercing resistance was gently decreased (the degree of decrease of the piercing resistance with respect to the length of the tapered portion 3 became greater toward 10D, and became smaller toward 20D), and the piercing resistance hardly changed above 20D.

From the above test results, the inventor of the present invention surmises the following. The resistance of the suture needle to the piercing through the artificial blood vessel is produced by the friction developing between the surface of the tapered portion 3 and the fibers of the artificial blood vessel when the tapered portion 3 pierces the tissue of the artificial blood vessel. Therefore, the piercing resistance is greatly influenced by the rate of increase of the cross-sectional area of the tapered portion 3 from the pointed end 4 (that is, the ratio of the length of the tapered portion 3 and the diameter of the main body portion 2).

From the above test results, it has been found that in order to decrease the piercing resistance, the length of the tapered portion 3 must be not less than 9D. From the viewpoint of the decrease of the piercing resistance, it is not significant to make the length of the tapered portion 3 more than 20D. Further, in view of the reduction of the cost required for grinding the needle material to form the tapered portion 3, preferably, the length of the tapered portion 3 should be less than 20D, and more preferably should be less than 15D particularly when it is important to reduce such grinding cost.

In the suture needle of the present invention, the length of the tapered portion 3 is smaller than two-thirds (⅔) of the overall length L of the suture needle.

The reason for this will now be described in detail. In order that the surgeon can stably grasp the suture needle through a needle holder 10 (FIG. 1), a pair of distal ends 10a and 10b of the needle holder 10 hold that portion of the suture needle spaced a distance of one-third (⅓) of its overall length L from the proximal end thereof (that is, a distance of two-thirds (⅔) from the pointed end 4). When the suture needle is to pierce the blood vessel, that portion of the suture needle held by the needle holder 10 is subjected to the maximum bending moment. Therefore, it is preferred to increase the cross-sectional area of that portion as much as possible so as to increase the bending strength thereof. In view of this, the length of the tapered portion 3 is decided to be less than ⅔ of the overall length L of the suture needle, so that that portion of the suture needle to be held or grasped by the needle holder 10 is included not in the tapered portion 3, but in the main body portion 2 which has the greatest cross-sectional area.

In currently-used suture needles, L is not less than 15D. In a suture needle with L=15D, there is provided (⅔)L=10D. Therefore, in such a suture needle, when the length of the tapered portion 3 is in the range of between not less than 9D and less than 10D, the above-mentioned two requirements can be met.

More strictly, it is preferred to take the width of the distal ends 10a and 10b of the needle holder 10 into consideration. The reason for this will now be described. Those portions of the suture needle with which those edges of the distal ends 10a and 10b of the needle holder 10 directed toward the pointed end 4 are respectively in contact are subjected to the maximum bending moment. Therefore, even if the center of each of the distal ends 10a and 10b of the needle holder 10 is disposed in registry with that portion (desired position) of the suture needle spaced a distance of (⅔)L from the proximal end thereof, that portion of the suture needle subjected to the maximum bending moment is displaced from the desired position a distance of a half (½) of the width of the distal end 10a (10b) toward the pointed end 4. Further, the surgeon roughly judges that portion of the suture needle spaced a distance of (⅔)L from the proximal end, with the eye, and then grasps that portion through the needle holder 10. Therefore, it is preferred to take into consideration the fact that the actual grasp position is not always exactly in registry with that portion of the suture needle spaced a distance of (⅔)L from the proximal end. For these reasons, it is preferred to determine the upper limit of the length of the tapered portion 3 by subtracting, from (⅔)L, the sum of the half of the width of the distal end 10a (10b) and the amount of the positional error of the actual grasp position. However, in the suture needle in which the length of the tapered portion is close to (⅔)L without taking the above factors into consideration, even if the surgeon grasps the rear end portion of the tapered portion 3 through the needle holder 10, no serious problem is encountered since the rear end portion of the tapered portion 3 is merely slightly smaller in cross-sectional area than the main body portion 2.

In most commonly-used suture needles, L is in the range of 35D to 40D. The above three sample groups A, B and C all fall within this range. In such most commonly-used suture needles, (⅔)L is in the range of 23.3D to 26.7D. Therefore, if the length of the tapered portion 3 is less than 20D, that portion of the suture needle subjected to the maximum bending moment can be disposed on the main body portion 2, even taking the width of the needle holder 10 and the error of the gasp position into consideration.

The diameter of the generally semi-spherical pointed end 4 of the suture needle is not more than 30 micron meters. The reason for this has been obtained from the following test. Among each of the above-mentioned three sample groups, two sample groups respectively having the tapered portion lengths of 3D and 12D were further selected. Thus, six sample groups were newly selected, and each of these six sample groups had five samples whose semi-spherical pointed ends 4 had the diameters of 10, 20, 30, 40 and 50 micron meters, respectively. The resistance of each suture needle of these six sample groups to the piercing through an artificial blood vessel was measured, and as a result it has been found that although the piercing resistance was low with the diameter of not more than 30 micron meters, the piercing resistance was extremely high above the diameter of 40 micron meters. From this fact, it is thought that with respect to the piercing resistance, the diameter of the semi-spherical pointed end 4 is closely related to the diameter of microscopic holes in the artificial blood vessel, that is, the fibril length thereof. Therefore, in order to ensure that the suture needle can have a good ability to pierce through the artificial blood vessel, the diameter of the semi-spherical pointed end 4 should be not more than 30 micron meters, and preferably about 20 micron meters. This dimension of the pointed end 4 is generally equal to the dimension of a pointed end of an ordinary suture needle usually used for a blood vessel of a living body, and therefore the suture needle of the present invention having the pointed end 4 of the above-mentioned diameter can also have a good ability to pierce into a blood vessel of a living body. Therefore, the suture needle which meets the above requirements of the tapered portion length and the above requirement of the diameter of the pointed end 4 is an optimum one for connecting the artificial blood vessel and the blood vessel of the living body together.

Next, the grasp portion 5 will now be described. The grasp portion 5 has the pair of grasp surfaces 5a and 5b disposed parallel to each other. The distal ends 10a and 10b of the needle holder 10 are held respectively against the grasp surfaces 5a and 5b, thereby grasping or holding the suture needle in a stable manner. The grasp portion 5 extends into the tapered portion 3. Therefore, the distal end portion of the suture needle passed through the blood vessel can be easily grasped. Also, when the surgeon holds the suture needle at the region thereof displaced greatly from that portion of the suture needle spaced a distance of one-third (⅓) of its overall length L from the proximal end thereof (though this is not desirable), this can be done easily.

The major proportion of the main body portion as well as the rear end portion of the tapered portion may have a square cross-section. In this case, the inner and outer surfaces of the curved configuration should be generally parallel to each other so as to serve as grasp surfaces.

The tapered portion of the suture needle is formed by grinding, and therefore when grinding the needle material (stock) of a very small diameter as is the case with the above-mentioned samples, it is difficult to make even the non-pressed portions exactly into a circular cross-section. Therefore, the tapered portion may have an oval or elliptical cross-section.

The rate of increase of the cross-sectional area of the tapered portion of the suture needle from the pointed end toward the main body portion may be constant. The suture needle does not always need to be curved, and may be straight. The needle material for the suture needle may be made of martensite-type stainless steel or precipitation hardened stainless steel. The gut-mounting hole may be disposed perpendicular to the axis of the suture needle. The suture needle may not have the pair of grasp surfaces.

What is claimed is:

1. A surgical suture needle of the taper point type including a proximal end portion defining a gut-mounting portion having a hole to which a gut is to be attached, a distal end portion defining a tapered portion whose cross-sectional area decreases progressively toward a distal end of said suture needle which is pointed, and an intermediate portion disposed between said gut-mounting portion and said tapered portion and defining a main body portion having a generally uniform cross-sectional area throughout an entire length thereof, the length of said tapered portion being in the range of between not less than 9D and less than 2/3L where D represents a diameter of an imaginary circle having the same cross-sectional area as that of said main body portion, and L represents the overall length of said suture needle.

2. A surgical suture needle according to claim 1, in which the length of said tapered portion is in the range of between not less than 9D and less than 20D.

3. A surgical suture needle according to claim 1, in which the length of said tapered portion is in the range of between not less than 9D and less than 15D.

* * * * *